United States Patent [19]

Lown et al.

[11] Patent Number: 5,502,068

[45] Date of Patent: Mar. 26, 1996

[54] CYCLOPROPYLPYRROLOINDOLE-OLIGOPEPTIDE ANTICANCER AGENTS

[75] Inventors: J. William Lown; Yuqiang Wang; Weide Luo, all of Edmonton, Canada

[73] Assignee: Synphar Laboratories, Inc., Alberta, Canada

[21] Appl. No.: 381,355

[22] Filed: Jan. 31, 1995

[51] Int. Cl.$^6$ .................. A61K 31/40; C07D 487/04
[52] U.S. Cl. .................. 514/397; 514/370; 514/377; 514/406; 514/410; 548/181; 548/233; 548/262.6; 548/265.4; 548/311.7; 548/364.7; 548/421
[58] Field of Search .................. 514/410, 370, 514/377, 397, 406; 548/421, 181, 233, 262.6, 265.4, 311.7364.7

[56] References Cited

U.S. PATENT DOCUMENTS

| | | | |
|---|---|---|---|
| 4,912,199 | 3/1990 | Lown et al. | 530/331 |
| 4,978,757 | 12/1990 | Kelly et al. | 548/421 |

FOREIGN PATENT DOCUMENTS

90/02746  3/1990  WIPO .................. C07D 519/00

OTHER PUBLICATIONS

Wang et al., Journal of Medicinal Chemistry, "CC–1065 Functional Analogues Possessing Different Electron–Withdrawing Substituents and Leaving Groups: Synthesis Kinetics, and Sequence Specificity of Reaction with DNA and Biological Evaluation", pp. 4172–4182, vol. 36, No. 26 (1993).

Wang et al., Heterocycles, "An Alternative Method for Synthesis of the CC–1065 Pharmacophore, 1,2,7,7a–Tetrahydrocycloprop[1,2–c]Indol–4–One", pp. 1399–1410, vol. 36, No. 6, (1993).

*Primary Examiner*—Jacqueline Haley
*Attorney, Agent, or Firm*—Nikaido, Marmelstein, Murray & Oram

[57] ABSTRACT

The invention is directed to novel cyclopropylpyrroloindole-oligopeptide compounds which are useful as anticancer agents. The novel cyclopropylpyrroloindole-oligopeptide compounds have the following general structure:

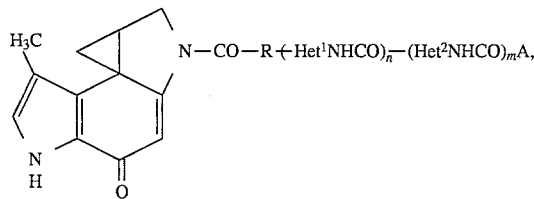

wherein,

Het$^1$ and Het$^2$ are individually selected from the group consisting of pyrrole, imidazole, triazole, thiophene, furan, thiazole, oxazole and pyrazole, R is selected from the group consisting of a valence bond; a $C_1$–$C_6$ alkyl; a $C_2$–$C_6$ alkenyl; a $C_2$–$C_6$ alkynyl; and an ortho, meta or para linked aromatic group, A is selected from the group consisting of a $C_1$–$C_6$ alkyl group; an amidine or derivative thereof; a guanidine; a secondary, tertiary or quaternary ammonium salt; and a sulfonium salt, n is 0 to 3, and m is 0 to 3.

20 Claims, 4 Drawing Sheets

CYCLOPROPYLPYRROLOINDOLE-OLIGOPEPTIDE ANTICANCER AGENTS

FIELD OF THE INVENTION

This invention relates to novel cyclopropylpyrroloindole-oligopeptides which are useful as anticancer agents.

BACKGROUND OF THE INVENTION

The title compounds are related to the family of natural oligopeptide antiviral antitumor antibiotics which include netropsin (Julia, M., Preau-Joseph, N. C. R., *Hebd-Seances, Acad. Sci.*, 1963, 257, 1115) and distamycin (Arcamone, F., Orezzi, P. G., Barbier, W., Nicolella, V., Penco, S., *Gazz. Chim. Ital.*, 1967, 97, 1097).

These structures contain pyrrole moieties connected by peptide bonds and with side chains, at least one of which is positively charged, i.e. an amidine group, N-formyl or a group of the guanidyl type.

Of this group of natural oligopeptide antibiotics only distamycin has been used as a therapeutic agent under the name of Stallimycin Hydrochloride in the form of a 1% cream, ointment or paste (Martindale, *The Extra Pharmacopoeia*, Twenty-eighth Edition, p. 825,1982) in treatments of infections produced by herpes simplex, herpes zoster and vaccinia viruses. The external use limitation of distamycin is due to its high cytotoxicity and a low therapeutic index which in the case of herpes viruses is about 3.

Other pertinent compounds are the natural product CC-1065 (Reynolds, V. L., Molineux, T. J., Kaplan, D., Swenson, D. H., Hurley, L. H., *Biochemistry*, 1985, 24, 6228), and the synthetic agent

CC-1065

FCE245517 (Arcamone, F. M., Animati, F., Barbieri, B., Configliacchi, E., D'Alessio, R., Geroni, C., Giulani, F. C., Lazzari, E., Menozzi, M., Mongetti, N., Penco, S., Verini, A., *J. Med. Chem.*, 1989, 32, 774.

FCE 24517

SUMMARY OF THE INVENTION

The title agents are compounds of the following general structure:

CPI—CO—R—(HetNHCO)$_n$—(HetNHCO)$_m$—A where

CPI =

R=CH$_2$ or CH$_2$CH$_2$ or —CH=CH— (Z or E), or —C≡C—; n=0 to 3, m=0 to 3, A is a moiety consisting of either an alkyl group, CH$_3$, CH$_3$CH$_2$, CH$_3$CH$_2$CH$_2$— or CH$_3$CH$_2$CH$_2$CH$_2$, or a group bearing a positive charge, e.g. amidine and derivatives, secondary, tertiary or quaternary ammonium salts, and sulfonium salts, Het is a monocyclic heterocyclic moiety, e.g. pyrrole, imidazole, triazoles, pyrazoles, thiazole, thiophene, furan, and oxazole. Zusammen (Z) and Entgegen (E) are recognized abbreviations designating configurations of alkene moieties (replacing cis and trans respectively). The title structure may contain one or more types of heterocycles in combination. This group of compounds exhibits anticancer activity in vitro against the human tumor KB cell line and the murine cell line P388 and in vivo anticancer activity against mice injected with P388 leukemia.

The title CPI-oligopeptides exhibit extremely high potencies against human tumor KB cells (Tables 1–3). In certain cases the cytotoxic potencies (TD$_{50}$ of ca. 10$^{-15}$M) exceed that of any other agent reported to date. They also have proven efficacy against i.p. implanted tumors in animals, affording increased life span of up to 57%. The title compounds in the latter tests showed no evidence of the delayed death syndrome that is the most serious limitation of drugs more directly related structurally to CC-1065. Thus CC-1065 proved to be too toxic for clinical usage, and analogs that may avoid the delayed death syndrome are currently undergoing clinical trials. FCE 24517 has similarly yet to obtain approval for clinical use.

Another distinct advantage of the title compounds over CC-1065, FCE 24517 and related structures is their ability to recognize and covalently bind to different DNA sequences (Tables 5, 6). CC-1065 and FCE 24517 are both strictly AT recognizing. Moreover FCE 24517 shows no evidence of DNA alkylation (Arcamone et al., 1989). In contrast the title compounds alkylate DNA strongly, like CC-1065, but unlike the latter are capable via the variable oligopeptide of recognizing and binding covalently to quite different sequences. This is of significance therapeutically since it has been demonstrated that clinically effective alkylators like cyclophosphamide, nitrosoureas and mitozolomide show marked DNA sequence selectivity for alkylation of the central guanine of runs of three or more guanines (Hartley, J. A., Gibson, N. W., Kohn, K. W., Mattes, W. B., *Cancer Research*, 1986, 46, 1943). Effective targeting of such G-rich regions of the genome, particularly some oncogenes may provide a basis for the unusual potency of such sequence-directed alkylators (Hartley, J. A., Lown, J. W., Mattes, W. B., Kohn, K. W., *Acta Oncologica*, 1988, 27, 503). The combination of the CPI alkylating moiety with the versatile DNA-sequence reading capability of the oligopeptide side-chain confers exceptional cytotoxic potency on these agents exceeding in the case of YW-059, for example, that of any other reported natural or synthetic agents.

DETAILED DESCRIPTION OF THE PREFERRED EMBODIMENTS

Compounds according to the present invention demonstrate anticancer activity. The following data summarized in Tables 1–3 documents the in vitro evidence for extremely high cytotoxic potency of the new CPI-oligopeptides against KB human nasopharengeal tumor cells. In the case of YW-059 (Table 2) the cytotoxic potency exceeds that of any other agent, natural or synthetic, reported to date. Table 3 presents cytotoxicity data on representative imidazole-bearing CPI-oligopeptides, i.e. capable of recognizing and binding covalently to mixed DNA sequences quite distinct from the strictly limited AATT recognition by either CC-1065 or FCE 24517. Table 4 presents animal data on the new drugs confirming significant anticancer activity is exhibited also in vivo.

TABLE 1

Cytotoxicity Data on New CPI-Oligopeptides

| Code Name | Structure | KB cells, toxicity $TD_{50}/\mu g\ mL^{-1}$ |
|---|---|---|
| YW-031 |  | $3.24 \times 10^{-5}$ |
| YW-032 |  | $3.8 \times 10^{-2}$ |
| YW-033 |  | $2.63 \times 10^{-1}$ |
| YW-034 |  | $2.75 \times 10^{-4}$ |
| YW-035 |  | $1 \times 10^{-3}$ |
| YW-036 |  | $4.71 \times 10^{-4}$ |
| Adriamycin | (No Structure) | $1.1 \times 10^{-2}$ |

TABLE 2

Cytotoxicity Data on New CPI-Oligopeptides

| Code Name | Structure | KB cells, toxicity $TD_{50}/\mu g\ mL^{-1}$ |
|---|---|---|
| YW-052 | (structure with CPI core, N-CO-CH=CH-pyrrole-NHCOC$_2$H$_7$) | $7.63 \times 10^{-10}$ |
| YW-053 | (structure with CPI core, N-CO-CH=CH-pyrrole-NHCO-pyrrole-NHCOC$_3$H$_7$) | $9.50 \times 10^{-10}$ |
| YW-059 | (structure with CPI core, N-CO-CH=CH-pyrrole-NHCOCH$_3$) | $1.5 \times 10^{-7}$* |
| CC-1065 | | $1 \times 10^{-6}$ |
| Adriamycin | No data | $5 \times 10^{-3}$ |

*Equivalent to $TD_{50}$ of ca. $10^{-15}$ M, i.e. the most potent cytotoxic agents ever reported.

TABLE 3

Cytotoxicity Data on New CPI-Oligopeptides

| Code Name | Structure | KB cells, toxicity $TD_{50}/\mu g\ mL^{-1}$ |
|---|---|---|
| YW-60 | (structure with CPI core, N-CO-pyrrole-NH-CO-CH$_2$-CH$_2$-N(CH$_3$)$_2$) | 0.184 |
| YW-61 | (structure with CPI core, N-CO-(pyrrole-NH-CO)$_2$-CH$_2$-CH$_2$-N(CH$_3$)$_2$) | 2.49 |

TABLE 3-continued

Cytotoxicity Data on New CPI-Oligopeptides

| Code Name | Structure | KB cells, toxicity $TD_{50}/\mu g\ mL^{-1}$ |
|---|---|---|
| YW-62 | [structure: CPI core with N-C(=O)-[pyrrole(N-CH3)-NH-C(=O)]3-CH2-CH2-N(CH3)2] | 1.37 |
| YW-63 | [structure: CPI core with N-C(=O)-imidazole(N-CH3)-NH-C(=O)-CH2-CH2-N(CH3)2] | 0.385 |
| YW-64 | [structure: CPI core with N-C(=O)-[imidazole(N-CH3)-NH-C(=O)]2-CH2-CH2-N(CH3)2] | 2.52 |
| Control Adrimycin | (No Structure) | 0.0044 |

TABLE 4

In vivo Anticancer Activity of CPI-Oligopeptides

| Compound | Chemical Structure | M.W. | In vivo ILS (%) P388 (ip) | Cytotoxicity $IC_{50}$ ($\mu g/mL$) (KB cell) |
|---|---|---|---|---|
| YW-34 | [structure: CPI-NC(=O)-CH=CH-pyrrole(N-CH3)] | 333.4 | 37.9 (1 mg/kg) | 0.00027 |
| YW-35 | [structure: CPI-NC(=O)-pyrrole(N-CH3)-NHC(=O)C2H5] | 379.4 | 56.5 (0.1 mg/kg) | 0.001 |

TABLE 4-continued

In vivo Anticancer Activity of CPI-Oligopeptides

| Compound | Chemical Structure | M.W. | In vivo ILS (%) P388 (ip) | Cytotoxicity IC$_{50}$ (μg/mL) (KB cell) |
|---|---|---|---|---|
| YW-36 | [structure] | 393.5 | 24.6 (1/7 cure) (0.3 mg/kg) | 0.00047 |

$^{1)}$Number of 30 day survivors is not included to calculate I.L.S. value.

Figures 1, 1A:
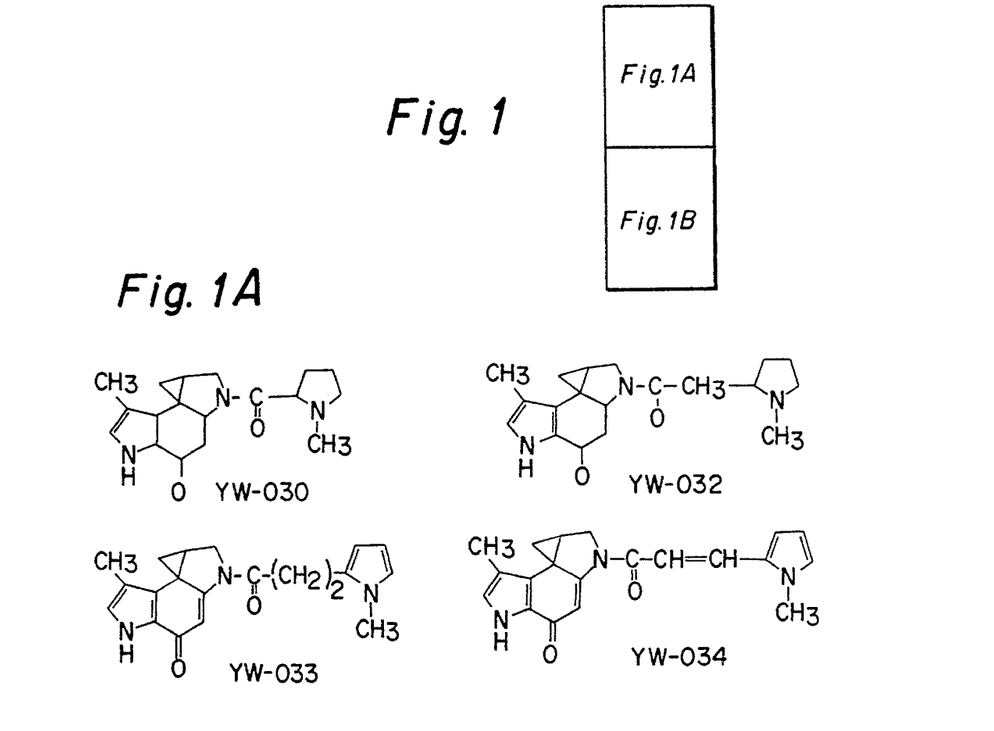
FIG. 1 shows the results of PAGE for YW-30, YW-32, YW-33, YW-34 and CC-1065.
Figure 1B:
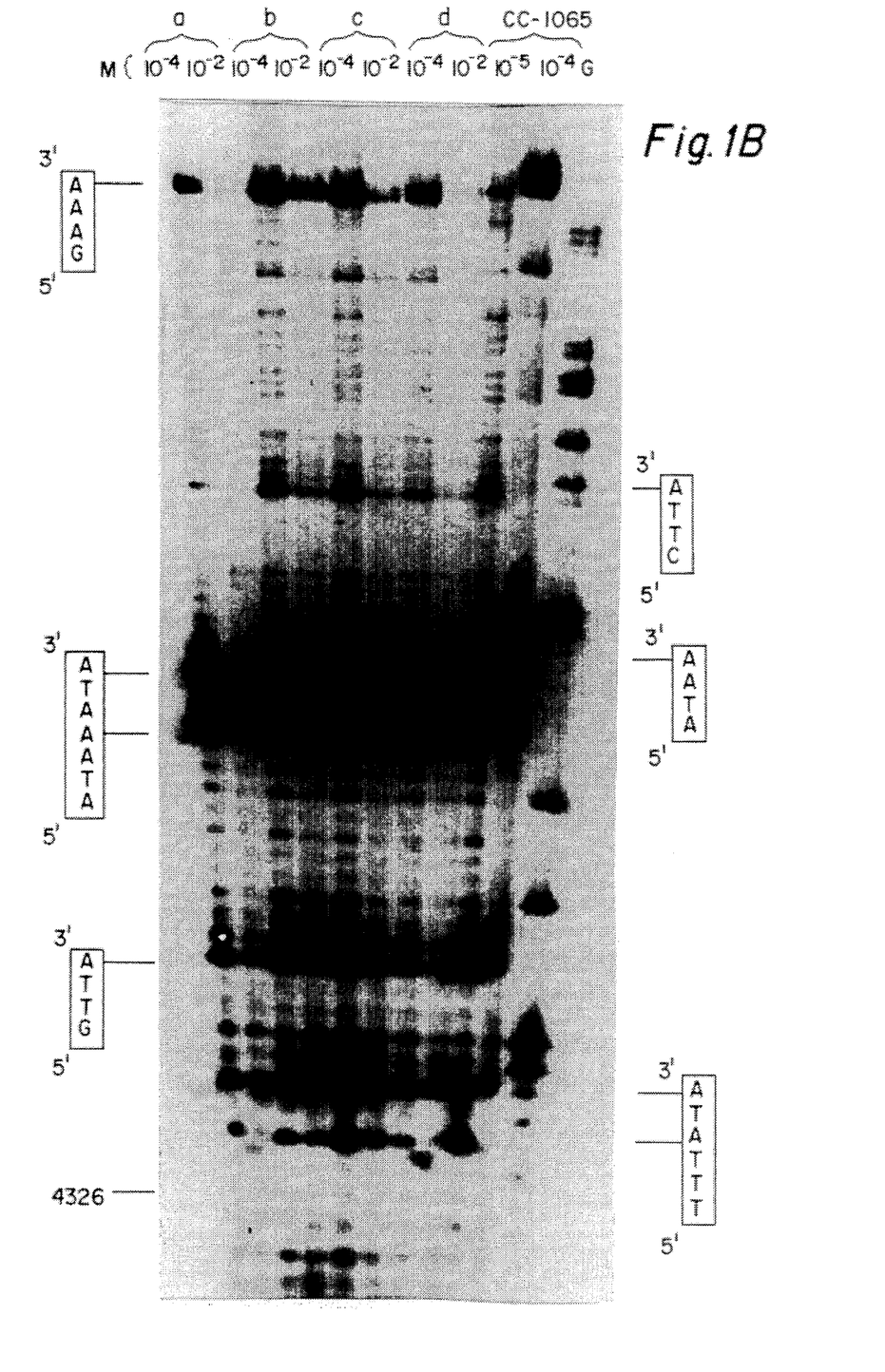
Figures 2, 2A:
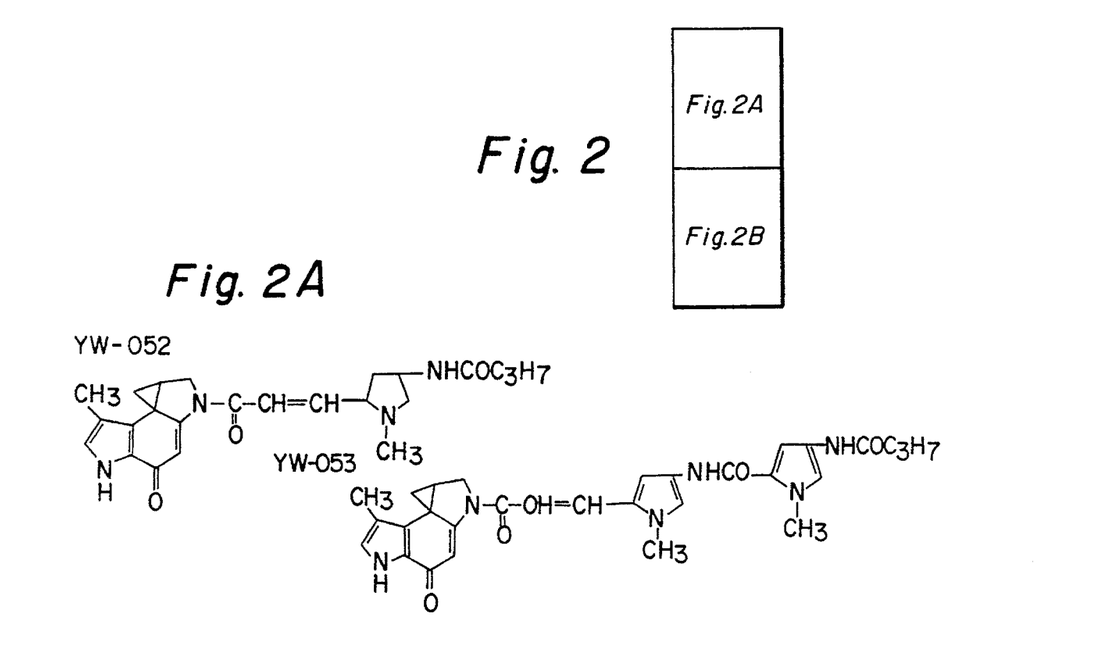
FIG. 2 shows the results of PAGE for CC-1065, YW-052 and YW-053.
Figure 2B:
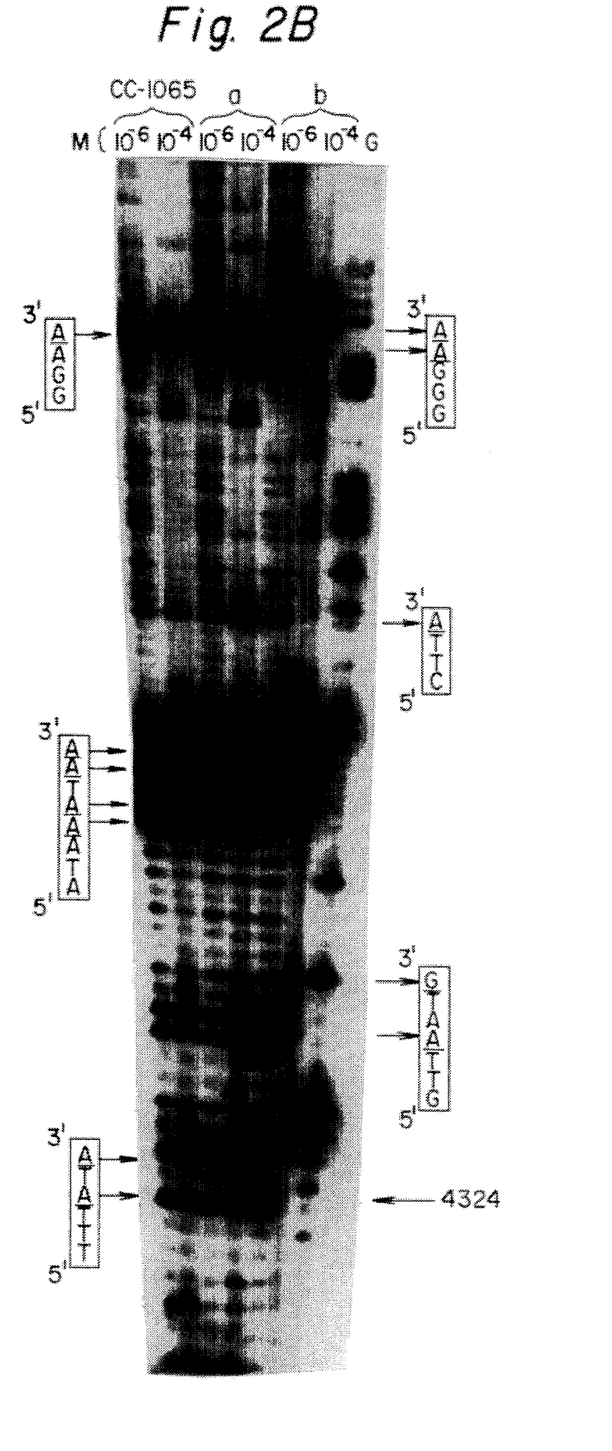
Figure 3:
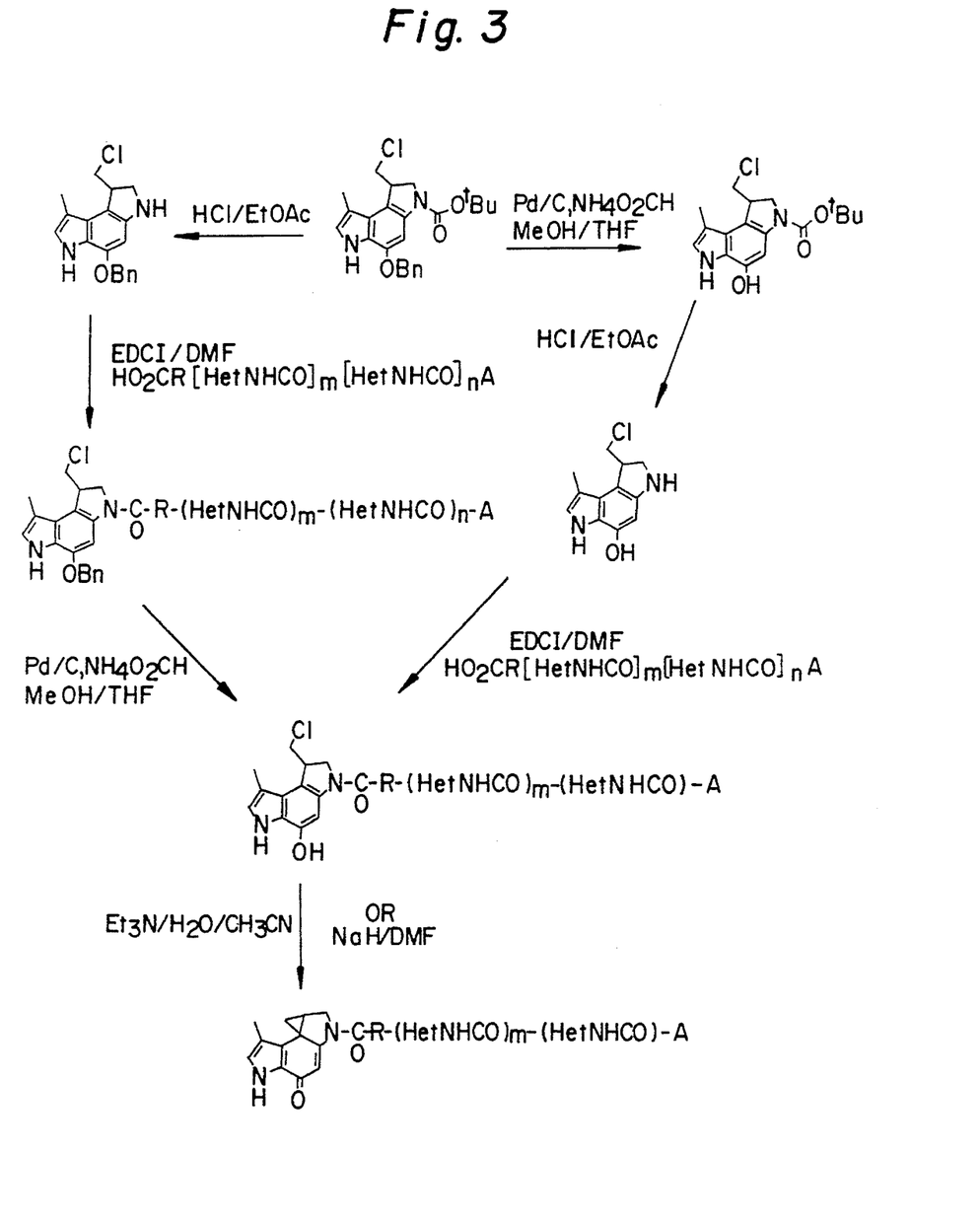
FIG. 3 shows synthetic routes for cyclopropylpyrroloindole-oligopeptide. anticancer agents.

In contrast to FCE 24517, clear evidence of site and sequence selective DNA alkylation was obtained for the new CPI-oligopeptides by polyacrylamide gel electrophoresis (PAGE). FIG. 1 displays the PAGE for YW-30, YW-32, YW-33, and YW-34 compared with CC-1065. Table 5 quantifies and compares the alkylation intensities at different sites for the CPI-oligopeptides with CC-1065. The PAGE results for some of the most potent drugs YW-052 and YW-053 are shown in FIG. 2 and tabulated for the primary and secondary alkylation sites in Table 6. A detailed analysis of the frequency of occurrence of bases flanking the prominent alkylation sites for YW-052 and YW-053 compared with CC-1065 is given in Table 7. These data provide evidence of the main cellular event that gives rise to the expression of anticancer properties of the new drugs and how they differ in detail from CC-1065.

TABLE 5

Summary of Alkylation Sites and Alkylation Intensity of CC-1065 and its Analogs

| Compound | Alkylation Intensity at: | | | | | | | | | |
|---|---|---|---|---|---|---|---|---|---|---|
| | ATAA* | AATA* | ATAA* | GATA* | TTAA* | GTTA | TATA | TTTA | CTTA | GAAA |
| CC-1065 | 1.47 | 1.08 | .96 | .80 | .80 | 1.20 | 1.02 | 1.09 | .61 | .35 |
| YW-30 | .76 | 1.27 | .85 | 1.38 | .55 | .95 | .83 | .50 | .44 | .66 |
| YW-32 | .88 | 1.35 | 1.01 | 1.35 | .71 | 1.03 | 1.05 | .63 | .61 | .79 |
| YW-33 | .95 | 1.42 | 1.11 | 1.41 | .84 | 1.27 | 1.40 | .97 | .68 | .84 |
| YW-34 | .71 | 1.30 | .84 | 1.09 | .52 | .73 | .77 | .49 | .44 | .55 |

*Denotes Alkylated adenines at 3' end

TABLE 6

Alkylation Sites of CC-1065 and its Analogs

| | Alkylation Sites* (5'–3') | |
|---|---|---|
| Compound | Strong | Moderate |
| CC-1065 | TTTA, GATA, ATAA, AATA, ATAA | TATA, TTAA, GTTA, CTTA, GGAA |
| YW-52 | TTTA, GATA, ATAA, AATA, ATAA | TATA, TTAA, GTTA, CTTA, ATGG, GGGA |
| YW-53 | TTTA, TATA, GTTA, AATA, ATAA | TTAA, AATG, GATA, ATAA, CTTA, GAAA |

*Alkylation sites are represented by underlined bases at the 3' end.

TABLE 7

Analysis of the DNA Sequence Flanking the Prominent Alkylation Sites of CC-1065 and its Analogs

| Com- pound | | Frequency of Occurrence (%) | | | | | | | |
|---|---|---|---|---|---|---|---|---|---|
| | | –3 | –2 | –1 | A* | G* | +1 | +2 | +3 |
| CC-1065 | A | 30 | 40 | 40 | 100 | 0 | 30 | 30 | 20 |
| | T | 30 | 60 | 60 | | | 50 | 30 | 30 |
| | G | 10 | — | — | | | 20 | 40 | 40 |
| | C | 30 | — | — | | | — | — | 10 |
| | A/T | 60 | 100 | 100 | | | 80 | 60 | 50 |
| YW-52 | A | 36 | 27 | 27 | 91 | 9 | 46 | 36 | 27 |
| | T | 27 | 64 | 55 | | | 36 | 37 | 27 |
| | G | 27 | 9 | 18 | | | 18 | 27 | 36 |
| | C | 10 | — | — | | | — | — | 10 |
| | A/T | 63 | 91 | 82 | | | 82 | 73 | 54 |
| YW-53 | A | 36 | 45 | 36 | 91 | 9 | 27 | 27 | 27 |
| | T | 27 | 55 | 64 | | | 45 | 27 | 27 |
| | G | 27 | — | — | | | 28 | 37 | 37 |
| | C | 10 | — | — | | | — | 9 | 9 |
| | A/T | 63 | 100 | 100 | | | 82 | 54 | 54 |

*Represents site of alkylation. Columns to the left and right of alkylated site(s) represent bases to the 5' and 3' sides, respectively.

The compounds of the present invention are useful as anticancer agents. An effective amount of one or more of the present compounds is administered to a patient preferably in the presence of a pharmaceutically acceptable carrier or diluent. Pharmaceutically compatible binding agents and/or adjuvant materials can also be included.

The compounds according to the present invention can be administered by any route, for example, orally, parenterally, intravenously, intradermally, subcutaneously, rectally or topically in a liquid or solid form. For injection purposes, the medium used may be a sterile liquid. As an injection medium, it is preferred to use water which contains conventional stabilizing agents, solubilizing agents and/or buffers. Desirable additives include but are not limited to tartrate and borate buffers, ethanol, dimethylsulfoxide, complex forming agents (for example ethylenediamine tetracetic acid), high molecular weight polymers (for example liquid polyethylene oxide) for viscosity regulation or polyethylene derivatives of sorbitan anhydrides. Solid carrier materials include but are not limited to starch, lactose, mannitol, methylcellulose, talc, highly dispersed silicic acid, high molecular weight fatty acids (for example stearic acid), gelatin, agar, calcium phosphate, magnesium stearate, animal and vegetable fats or solid high molecular weigh polymers (for example polyethylene glycol).

The present compounds can be administered in dosages and amounts which are conventional in the art. The compounds can be used at a dosage range of about 1–200 mg/kg total body weight/day. The dosages may be administered at once or may be divided into a number of smaller doses to be administered at varying intervals of time.

Preferred embodiments of the invention are exemplified in the following examples which are in no way to be construed as limiting the scope of the present invention.

EXAMPLE 1

1, 2, 8, 8a-Tetrahydro-7-methyl-2-(4-butyramido-N-methyl-2-pyrroleacryloyl)-cyclopropa[c]-pyrrolo[ 3, 2, e]indole-4-(5H)-one (CP7-19)

Compound CP7-19 of the formula X, where R=trans-CH=CH; Het=N-methylpyrrole; m=1; n=0; A=Butyramido, was prepared. 10% Pd/C(30 mg) and ammonium formate (30 mg) were added to 5-benzyloxy-3 -tert-butyloxycarbonyl-1-chloromethyl-8-methyl-1,2-dihydro-3H-pyrrolo [3,2-e]indole (30 mg), which was synthesized using the reported methods (Ref. D. L. Boger and R. S. Coleman, *J. Am. Chem. Soc.* 1988, 110, 4796–4807), dissolved in a solution of tetrahydrofuran and methanol (0.8 ml, 1/1, v/v) and the reaction mixture was stirred at room temperature for 20 min. The solid was removed by filtration and water (2 ml) was added. The product was extracted with ethyl acetate (10 ml×3) and the organic phase was dried over sodium sulfate. The solvent was removed in vacuo to generate an oil CP7-13. Without further purification, the oil CP7-13 was treated with anhydrous 3N hydrochloric acid in ethyl acetate (3 ml) at room temperature for 40 min. The solvent was removed in vacuo to give an unstable intermediate, CP7-14.

Without further purification, CP7-14 was dissolved in dimethylformamide (1 ml) under nitrogen. 4-Butyramido-N-methyl-2-pyrroleacrylic acid (CP7-6) (16.6 mg) and 1-[(3-dimethylamino)propyl]-3-ethylcarbodiimide hydrochloride (67.6 mg) were added sequentially. The reaction mixture was stirred in dark at room temperature for 2 days. The mixture was purified on silica plate eluting with a mixture of acetone and ethyl acetate (1:1, v/v) to give an unstable CP7-17. Without further purification, CP7-17 was dissolved in a mixture of acetonlerile, triethylamine and water (0.6 ml of each) and the reaction mixture was stirred for 30 min under nitrogen. The solvent was removed by a high vacuum pump and the residue was dissolved in acetone. The mixture was then purified on a silica plate eluting with a mixture of acetone and ethyl acetate (1:1, v/v). 9:4 mg (32 % yield) of a yellow powder was obtained. $^1$H NMR (acetone-d6, ppm): 10.48 (br s, 1H, NH), 8.97 (br s, 1H, NH), 7.63– 7.58 (d, 1H, J=15.5 Hz, C$\underline{H}$CH), 7.34 (d, 1H, J=2.0 Hz, C5'-H), 6.88 (br m, 1H, C6-H), 6.72 (br s, 1H, C3-H), 6.67 (d, 1H, J=2.0 Hz, C3'-H), 6.58–6.62 (d, 1H, J=15.5 Hz, CHC$\underline{H}$), 4.31–4.27 (d, 1H, J=10.5 Hz, NC$\underline{H}$), 4.21–416 (dd, 1H, J=4.5, 10.5 Hz, NCH$\underline{H}$), 3.76 (s, 3H, NCH$_3$), 3.08–3.03 (m, C8a-H), 2.27–2.21 (t, 2H, J=7.5 Hz, CH$_3$CH$_2$ C$\underline{H}_2$), 1.97– 1.93 (dd, 1H, J=4.5, 7.5 Hz, C8-H$\underline{H}$), 1.7–1.59 (m, 2H, CH$_3$ C $\underline{H}_2$CH$_2$), 1.28–1.25 (t, 1H, J=4.5 Hz, C8-H$\underline{H}$), 0.94–0.89 (t, 3H, J=7.5 Hz, C$\underline{H}_3$CH$_2$CH$_2$). FABHRMS calcd for C$_{24}$H$_{26}$N$_4$O$_3$H 419.2083, found 419.2092 (100%).

EXAMPLE 2

1, 2, 8, 8a-Tetrahydro-7-methyl-2-[4-(4-butyramido-N-methyl-2 -pyrrolecarboxyamido)-N-methyl-2-pyrroleacryloyl-)cyclopropa[c]-pyrrolo[3, 2,]indole-4-(5H)-one (CP7-20)

Compound CP7-20 of the formula X, where R=trans-CH=CH; Het=N-methylpyrrole; m=2; n=0; A=butyramido, was prepared from 5-benzyloxy- 3-tert-butyloxycarbonyl-1-chloromethyl-8-methyl-1,2-dihydro- 3H-pyrrolo[3,2-e]indole (30 mg) and 4-(4-butyramido-N-methyl-2-pyrrolecarboxyamido)-N-methyl-2-pyrroleacrylic acid (25 mg) using the same method as described for CP7-19. The product is a yellow powder (15% yield). $^1$H NMR (acetone-d6, ppm): 10.54 (br s, 1H, NH), 9.25 (br s, 1H, NH), 8.97 (br s, 1H, NH), 7.64–7.60 (d, 1H, J=15.5 Hz, C$\underline{H}$CH), 7.42 (d, 1H, J=2.0 Hz, C5'-H), 7.17 (d, 1H, J=2.0 Hz, C5'-H), 6.89 (br m, 1H, C6-H), 6.83 (d, 1H, J=2.0 Hz, C3'-H), 6.80 (d, 1H, J=2.0 Hz, C3"-H), 6.73 (br s, 1H, C3-H), 6.58–6.63 (d, 1H, J=15.5 Hz, CHC$\underline{H}$), 4.32–4.28, (d, 1H, J=10.5 Hz, NC$\underline{H}$H), 4.22–4.17 (dd, 1H, J=4.5, 10.5 Hz, NCH$\underline{H}$), 3.90 (s, 3H, NCH$_3$), 3.78 (s, 3H, NCH$_3$), 3.09–3.03 (m, C8a-H), 2.25–2.20 (t, 2H, J=7.5 Hz, CH$_3$CH$_2$CH$_2$), 1.97–1.94 (dd, 1H, J=4.5, 7.5 Hz, C8-H$\underline{H}$), 1.70–1.58 (m, 2H, CH$_3$CH$_2$CH$_2$), 1.29–1.27 (t, 1H, J=4.5 Hz, C8-H$\underline{H}$), 0.94–0.89 (t, 3H, J=7.5 Hz, C $\underline{H}_3$CH$_2$CH$_2$). FABHRMS calcd for C$_{30}$H$_{32}$N$_6$O$_4$H 541.2563, found 541.2563 (100%).

EXAMPLE 3

1, 2, 8, 8a-Tetrahydro-7-methyl-2-(N-methyl-2-pyrroleacetoxy)cyclopropa-[c]-pyrrolo [ 3, 2, e]indole-4-(5H)-one (CP5-13).

Compound CP5-13 of the formula X, where R=CH$_2$;Het=N-methylpyrrole; m=1; n=0; A=H, was prepared. 5-Benzyloxy-3 -tert-butyloxlycarbonyl-1-chloromethyl-8-methyl-1, 2-dihydro-3H-pyrrolo[3,2-e]indole (10 mg, 23 umol) was dissolved in 3N HCl in ethyl acetate (2 ml) and the solution was stirred at ambient temperature for 40 min. The solvent was removed and dichloromethane (2 ml) was added. Dichloromethane was removed and the residue was dissolved in dimethylformamide (0.5 ml). N-methyl-2-pyrroleacetic acid (5 mg, 36 umol), 1-(3-dimethylaminopropyl)-3-ethylcarbodiimide hydrochloride (40 mg, 208 umol) and sodium hydrogen carbonate (10 mg) were added sequentially. The reaction mixture was stirred at ambient temperature overnight and then purified by flash column chromatography eluting with a mixture of ethyl acetate and hexane (1:3 to 1:1, v/v). White solid CP5-9 (10.2 mg, 22.8 umol, 97%): mp 188°–190 0° C.; $^1$H NMR (CDCl$_3$): 8.18 (br s, 1H, NH), 8.04 (s, 1H, C4H), 7.47–7.34 (m, 5H, C$_6$H$_5$), 6.96 (s, 1H, C7-H), 6.63(s, 1H, C5'-H), 6.10 (s, 2H, C3'-H, C4'-H), 5.22–5.13 (g, 2H, J=3.0, 12 Hz, C$_6$H$_5$C$\underline{H}_2$O), 4.45–4.41 (d, 1H, J=11.0 Hz, NCH$\underline{H}$), 4.0–3.93 (m, 1H, CH$_2$ClC$\underline{H}$CH$_2$), 3.85–3.80 (m, 3H, COCH$_2$, C$\underline{H}$HCl), 3.70 (s, 3H, NCH$_3$), 3.40–3.33 (t, 1H, J=10.5 Hz, CH$\underline{H}$Cl), 2.40 (s, 3H, ArCH$_3$); EIHRMS calcd for C$_{26}$H$_{26}$ClN$_3$O$_2$, 447.1716 found 447.1708, was obtained.

To a solution of CP5-9 (5.1 mg, 11.4 umol) in methanol and THF (0.6 ml, 1:1, v/v) was added ammonium formate (10 mg) and 10% Pd/C (10 mg) and the reaction mixture was stirred at ambient temperature for 20 min. The mixture was filtered and the filtrate was extracted with ethyl acetate (10 ml×2). The solvent was removed in vacuo. To the residue were added acetonitrile (1 ml), triethylamine (0.2 ml) and water (0.2 ml) and the solution was stirred at ambient temperature for 30 min. The solvent was removed and the salt in the flask was washed away using water (2 ml×3). The flask was dried and ether was added. The solid product was collected and washed with more ether. 1.5 mg (4.67 mmol, 41% yield) of a gray powder was obtained: $^1$H NMR (acetone-d6): 6.87 (s, 1H, C6-H), 6.62–6.60 (t, 1H, J=2.0 Hz, C5'-H), 5.91–5.89 (t, 1H, J=3.0 Hz, C4'-H), 5.88–5.86 (m, 1H, C3'-H), 4.32–4.29 (d, 1H, J=11.0 Hz, NCH$\underline{H}$), 4.21–4.16 (m, 1H, NCH$\underline{H}$), 3.88–3.86 (d, 2H, J=5.0 Hz, COCH$_2$), 3.56 (s, 3H, NCH$_3$), 3.08–3.04 (m, 1H, C8a-H), 2.01 (d, 3H, J=1.0 Hz, ArCH$_3$), 1.92–1.88 (dd, 1H, J=4.0, 7.0 Hz, C8-H$\underline{H}$), 1.23I..20 (t, 1H, J=4.5 Hz, C8-H$\underline{H}$); EIHRMS calcd for C$_{19}$H$_{19}$N$_3$O$_2$, 321.1479 found 321.1462.

EXAMPLE 4

1, 2, 8, 8a-Tetrahydro-7-methyl-2-(N-methyl-2-pyrrolepropionyloxy)cyclopropa[c]-pyrrolo[3, 2, e]indole-4-(5H)-one (CP5-14).

Compound CP5-14 of the formula X, where R=CH$_2$CH$_2$; Het=N-methylpyrrole; m=1; n=0; A=H, was prepared. Using the same method as described for CP5-9, from 5-benzyloxy-3-tert-butyloxycarbonyl- 1-chloromethyl-8-methyl-1,2-dihydro-3H-pyrrolo[3,2-e]indole and N-methyl-2-pyrrolepropionic acid, 5-benzyloxy-1,2-dihydro- 1-chloroxymethyl-8-methyl-3(N-methyl-2-pyrrolepropionyloxy)-3H-pyrrolo[3, 2-e]indole (CP5-10) was synthesized in the yield of 60% as a white solid: mp 159°–161° C.; $^1$H NMR (acetone-d6): 8.09 (s, 1H, C4-H), 7.58–7.30 (m, 5H, C$_6$H$_5$), 7.08 (s, 1H, C7-H), 6.56–6.55 (t, 1H, J=2.0 Hz, C5'-H), 5.90–5.88 (dd, 1H, J=0.5, 2.5 Hz, C4'-H), 5.88–5.86 (m, 1H, C3'-H), 5.23 (s, 2H, C$_6$H$_5$C$\underline{H}_2$O), 4.30–4.18 (m, 2H, NCH $_2$), 4.33–3.96 (m, 1H, CH$_2$ClCHC$_2$), 3.89–3.84 (dd, 1H, J=2.5,10.5 Hz, C $\underline{H}$HCl), 3.70 (s, 3H, NCH$_3$), 3.53–3.46 (t, 1H, J=10.,5 Hz, CH$\underline{H}$Cl), 2.96–2.79 (m, 4H, CH$_2$CH$_2$), 2.40 (s, 3H, ArCH$_3$); EIHRMS calcd for C$_{27}$H$_{28}$ClN$_3$O$_2$, 461.1873 found 461.1873.

By the treatment of CP5-10 in a similar procedure as described for CP5-13 except that sodium hydride in N,N-dimethylformamide (0.2 ml) and tetrahydrofuran (0.8 ml) was used for the final cyclization reaction, 46% yield of a grey solid CP5-14 was obtained: $^1$H NMR (DMF-d6): 6.95(s, 1H, C6-H), 6.66–6.64 (t, 1H, J=2.0 Hz, C5'-H), 5.90–5.88 (t, 1H, J=3.0 Hz, C4'-H), 5.85–5.82(m, 1H, C3'-H), 4.26–4.22 (d, 1H, J=11.0 Hz, NCH$\underline{H}$), 4.20–4.17 (m, 1H, NCH$\underline{H}$), 3.60 (s, 3H, NCH$_3$), 3.15–2.90 (m, 1H, C8a-H), 2.30 (d, 3H, J=1.0 Hz, ARCH$_3$), 1.94–1.90 (dd, 1H, J=4.0, 7.0 Hz, C8-H$\underline{H}$), 1.25–1.22 (t, 1H, J=4.5 Hz, C8-H$\underline{H}$); EIHRMS calcd for C$_{20}$H$_{21}$N$_3$O$_2$, 335.1636 found 335.1618.

EXAMPLE 5

1, 2, 8, 8a-Tetrahydro-7-methyl-2-(4-acetamido-N-methyl-2-pyrrolecarboxy) cyclopropa[c]-pyrrolo (3, 2, e]indole-4-(5H)-one (CP4-19).

Compound CP4-19 of the formula X, where R=0; Het=N-methylpyrrole; m=1; n=0; A=acetamido, was prepared. 5-Benzyloxy-3-tert-butyloxycarbonyl-1-chloromethyl-8-methyl,2-dihydro-3H-pyrrolo[3,2-e]indole (20 mg, 47 umol) was dissolved in 3N HCl in ethyl acetate and the solution was stirred at ambient temperature for 40 min. The solvent was removed and dichloromethane (2 ml) was added. Dichloromethane was removed and the residue was dissolved in dimethylformamide (1 ml). 4-Acetamido-N-methyl-2-pyrrolecarboxylic acid (CP4-5) (10.2 mg, 56 umol), 1-(3-dimethylaminopropyl)-3-ethylcarbodiimide hydrochloride (45 mg, 234 umol) and sodium hydrogen carbonate (20 mg) were added sequentially. The reaction mixture was stirred at ambient temperature overnight and then purified by flash column chromatography using ethyl acetate as an eluent. A grey powder (18.4 mg, 80% yield) was obtained as product CP4-11: mp 143°–145 ° C.; $^1$H NMR (500 MHz, CDCl$_3$): 8.15 (br s, 1H, NH), 8.00 (br s, 1H, NH), 7.60 (br s, 1H, C4-H), 7.43–7.32 (m, 7.24 (s, 1H, C5'-H), 6.97 (s, 1H, C7-H), 6.42 (s, 1H, C3'-H), 5.22–5.11 (q, 2H, J=6.6, 25.8 Hz, PhCH$_2$O), 4.52–4.50 (d, 1H, NCH$\underline{H}$, J=6.6 Hz), 4.31–4.27 (dd, 1H, J=4.8, 6.6 Hz, NCH$\underline{H}$), 3.83–3.78 (m, 5H, C$\underline{H}$HCl, CH$_2$ClC$\underline{H}$CH$_2$, NCH$_3$), 3.42–3.38 (t, 1H, J=6.6 Hz, CHH$\underline{H}$Cl), 2.40 (s, 3H, ArCH$_3$), 2.17 (s, 3H, CH$_3$CO); EIHRMS calcd for C$_{27}$H$_{27}$N$_4$O$_{Cl}$, 490.1774, found 490.1765.

To a solution of CP4-11 (20.6 mg, 42 umol) in methanol and tetrahydrofuran (0.6 mi. 1:1, v/v) was added ammonium formate (20 mg) and 10% Pd/C (20 mg) and the reaction mixture was stirred at ambient temperature for 20 min. The mixture was filtered and water (3 ml) was added to the filtrate. The mixture was extracted with ethyl acetate (10 ml×2). The solvent was removed in vacuo. To the residue were added acetonitrile (0.4 ml), triethylamine ( 0.2 ml) and water (0.2 ml) and the solution was stirred at ambient temperature for 20 min. The solvent was removed and the salt in flask was washed away using water (2 ml×3). Ethyl ether was added and the solid product was collected and washed with more ether. A gray powder product (10.5 mg, 69% yield) was obtained: $^1$H NMR (acetone-d6): 10.10 (br s, 1H, NH), 8.74 (br s, 1H, NH), 7.28 (s, 1H, C5'-H), 6.82 (s, 1H, C6-H), 6.45 (s, 1H, C3'-H), 6.17 (s, 1H, C3-H), 4.22–4.17 (dd, 1H, NCH$\underline{H}$, J=4.5, 11 Hz), 4.08–4.05 (d, 1H, J=11 Hz, NCH$\underline{H}$), 3.77 (s, 3H, NCH$_3$), 2.93–2.87 (m, 1H, C8a-H), 2.02–1.97 (m, 7H, ArCH$_3$, CH$_3$CO, C8-H$\underline{H}$), 1.40–1.33 (q, 1H, J=5.0, 10 Hz, C8-H$\underline{H}$), EIHRMS calcd for C$_{20}$H$_{20}$N$_4$O$_3$, 364.1537, found 364.1580.

EXAMPLE 6

1, 2, 8, 8a-Tetrahydro-7-methyl-2-{4-{4-[4-( 3-dimethylaminopropionamido)-N-methylpyrrole- 2-carboxyamido}-N-methylpyrrole-2carboxyamido}-N-methylpyrrole-2-carboxy }cyclopropa[c]-pyrrolo[3, 2, e]indole-4-(5H)-one (CP3-38)

Compound CP3-38 of the formula X, where R=0; Het= N-methylpyrrole; m=3; n=0; A=3-dimemethylaminopropionamido, was prepared. Pd/C (25 mg) and ammonium formate (25 mg, 397 umol) were added to 5-benzyloxy-3-tert-butyloxycarbonyl-1-chloromethyl-8 -methyl-1,2-dihydro-3H-pyrrolo[3,2-e]indole (CP3-28, 20 mg, 47 umol) dissolved in a solution of tetrahydrofuran and methanol (0.6 ml, 1/1, v/v) and the reaction mixture was stirred at room temperature for 20 min. The solid was removed by filtration and water (2 ml) was added to the filtrate. The mixture was extracted with ethyl acetate (5 ml×3) and the organic phase was dried over sodium sulfate. The solvent was removed in vacuo and a colorless solid, CP3-29, was obtained. Without further purification, CP3-29 was treated with anhydrous 3N hydrochloric acid in ethyl acetate at room temperature for 40 min. The solvent was removed in vacuo to give an unstable CP3-30. Dimethylformamide (0.8 ml), sodium hydrogen carbonate (21 mg, 250 umol), 4-{4-[4(3 -dimethylaminopropionamido)-N-methylpyrrole-2-carboxyamido]-N-methylpyrrole -2-carboxyamido}-N-methylpyrrole-2-carboxylic acid (CP3-20) (21 mg, 50 umol) and 1-[(3dimethylamino-)propyl]3-ethylcarbodiimide hydrochloride (48 mg, 250 umol) were added sequentially to CP3-30 under nitrogen. The reaction mixture was stirred in the dark at room temperature overnight. The product CP3-33 was purified on silica gel plate using methanol and acetone (⅓, v/v) as an eluent and washed off the silica using dimethylformamide and tetrahydrofuran (¼, v/v). 8 mg ( 11 umol, 23% yield) of unstable 31 was obtained. To a solution of CP3-33 (8 mg, 11 umol) in dimethylformamide and tetrahydrofuran (0.8 ml, ⅓, v/v) was added sodium hydride (4 mg, 100 umol, 60% dispersion in mineral oil) at 0° C. under nitrogen. The reaction mixture was stirred at 0° C. for 1 h. The product was purified on silica gel plate using methanol and acetone (⅓, v/v) as an eluent and washed off the silica gel using dimethylformamide and tetrahydrofuran (¼, v/v). The product CP3-38 (2.7 mg, 4 umol, 32% yield) was obtained: $^1$H NMR (DMF-d$_7$): 11–50 (s, 1H, NH), 10.10 (s, 1H, NH), 10.02 (s, 1H, NH), 9.97 (s, 1H, NH), 7.55 (d, 1H, J=1.8 Hz, py-CH), 7.31 (d, 1H, J=1.8 Hz, py-CH), 7.23 (d, 1H, J=1.8 Hz, py-CH), 7.20 (d, I H, J=1.8 Hz, py-CH), 6.97–6.95 (m, 2H, C6-H, py-CH), 6.82 (d, 1H, J=1.8 Hz, py-CH), 6.23 (s, 1H, C3-H), 4.33–4.28 (dd, 1H, J=4.5, 11.0 Hz, C1-H$\underline{H}$), 4.18–4.15 (d, 1H, J=11.0 Hz, C1-H$\underline{H}$), 3.95 (s, 3H, NCH$_3$), 3.92 (s, 3H, NCH$_3$), 3.83 (s, 3H, NCH$_3$), 3.10 (m, 1H, C8a-H), 2.57– 2.54 (t, 2H, J=6.0 Hz, COCH$_2$), 2.43–2.39 (t, 2H, J=6.0 Hz, CH$_2$N), 2.18 [s, 6H, 2XNCH$_3$, 2.05 (s, 3H, ArCH$_3$), 2.0 (m, partially obscured by ArCH$_3$, 1H, C8-H$\underline{H}$), 1.43–1.41 (t, 1H, J=4.5 Hz, C8-H$\underline{H}$); FABHRMS calcd for C$_{35}$H$_{39}$N$_9$O$_5$ (M+H) 666.3152, found 666.3156.

EXAMPLE 7

1, 2, 8, 8a-Tetrahydro-7-methyl-2-{4-[4-(3 -dimethylaminopropionamido)-N-methylimidazole-2-carboxyamido]-N-methylimidazole- 2-carboxy}-cyclopropa[c]pyrrolo[3,2,e]indole-4-(5H)-one (CP3-40).

Compound CP3-40 of the formula X, where R=0; Het= N-methylimidazole; m=2; n 0; A=3-dimethylaminopropionamido, was prepared from4-[4-(3-dimethylaminopropionamido)-N-methylimidazole-2 carboxamido]-N-methylimidazole-2-carboxylic acid and 5-benzyloxy-3-tert-butyloxycarbonyl-1-chloromethyl-8-methyl-1,2-dihydro-3H-pyrrolo [3,2-e]indole CP3-28 using the same procedure as that described for CP3-38 (13% yield from CP3-28). $^1$H NMR (DMF-d$_7$): 11.55 (s, 1H, NH), 10.65 (s, 1H, NH), 9.64 (s, 1H, NH), 7.69 (s, 1H, im-CH), 7.56 (s, 1H, im-CH), 7.00 (d, 1H, J=2.0 Hz, C6-H), 6.97 (s, 1H, C3-H), 4.84–4.80 (d, 1H, J=11.0 Hz, C1-H$\underline{H}$), 4.54–4.48 (dd, 1H, J=11.0 Hz, C1-H$\underline{H}$, 4.09 (s, 3H, NCH$_3$), 4.00 (s, 3H, NCH$_3$), 3.20 (m, 1H, C8a-H), 2.61–2.56 (m, 4H, CH$_2$CH$_2$), 2.20 [s, 6H, 2XNCH$_3$, 2.05 (s, 3H, ArCH$_3$), 2.02–1.98 (dd, 1H, C8-H$\underline{H}$, J=4.5, 7.5 Hz), 1.41–1.38 (t, 1H, C8-H$\underline{H}$, J=4.5 Hz); FABHRMS calcd for C$_{27}$H$_{32}$N$_9$O$_4$(M+H) 546.2577, found 546.2583.

EXAMPLE 8

1, 2, 8, 8a-Tetrahydro-7-methyl-2-[4-(4 -butyramido-N-methoxymethylpyrrole-2-carboxyamido)-N-methoxymethylpyrrole-2-carboxyl]cyclopropa[c]-pyrrolo[3, 2-e]indole-4-(5H)-one (CP8-26)

Compound CP8-26 of the formula X, where R=0; Het= N-methoxymethylpyrrole; m=2; n=0; A=butyramido, was prepared. 5-Benzyloxy-3-tert-butyloxycarbonyl-1-chloromethyl-8-methyl-1,2 -dihydro-3H-pyrrolo [3,2-e]indole CP8-14 (33 mg, 77.5 umol) was dissolved in 3N HCl in ethyl acetate (3 ml) and the solution was stirred at ambient temperature for 40 min. The solvent was removed and dichloromethane (2 ml) was added. Dichloromethane was removed and the residue was dissolved in dimethylformamide (1 ml). 4-(4-butyamido-N-methoxymethylpyrrole-2 -carboxamido)-N-methoxymethylpyrrole-2-carboxylic acid CP8-11 (31 mg, 79.2 umol), 1-(3-dimethylaminopropyl)-3-ethylcarbodiimide hydrochloride (74 mg) and sodium hydrogen carbonate (15 mg) were added sequentially. The reaction mixture was stirred at ambient temperature overnight and then purified by flash column chromatography using ethyl acetate and hexane (2: 1, v/v) as an eluent to afford 5-benzyloxy-1 -chloromethyl-8-methyl-3-[4-(4-butyramido-N-methoxymethylpyrrole-2 -carboxyamido)-N-methoxymethylpyrrole-2-carboxy]-1, 2-dihydro-3H-pyrrolo[3, 2-e]indole CP8-18 (38 mg, 54 umol, 70% yield): $^1$H NMR (CDCl$_3$): 8.57 (br s, 1H, NH), 8.35 (br s, 1H, NH), 7.64–7.33 (m, 8H, C4-H, 2×Py-H, C$_6$H$_5$), 6.94 (s, 1H, C7-H), 6.70 (s, 1H, Py-H), 6.57 (s, 1H, Py-H) 5.71–5.67 (d, 1H, J=9.0 Hz, C$\underline{H}$HOCH$_3$), 5.53 (s, 2H, CH$_2$OCH$_3$) 5.22–5.05 (m, 3 H, CH$\underline{H}$OCH$_3$,PhCH$_2$O), 4.48–4.44 (d, 1H, NCH$\underline{H}$, J=11.0 Hz), 4.27–4.21 (t, 1H, J=9.5 Hz, NCH$\underline{H}$), 3.79–3.71 (m, 2H, C$\underline{H}$HCl, CH$_2$ClC$\underline{H}$CH$_2$), 3.39–3–33 (m, 4H, CH$\underline{H}$Cl OCH$_3$), 3.25 (s, 3H, OCH$_3$), 2.38 (s, 3H, ArCH$_3$), 2.282–2.24 (t, 2H, J=7Hz, CH$_3$CH$_2$ C$\underline{H}_2$), 1.73–1–64 (m, 2H, CH$_3$CH$_2$CH$_2$), 0.97–0.92 ( t, 3H, J=7 Hz, C$\underline{H}$ $_3$CH$_2$CH$_2$. FABHRMS calcd for C$_3$H$_{40}$N$_6$O$_6$ClH 700.2776, found 700.2723.

To a solution of CP8-18 (38 mg, 54 umol) in methanol and THF (0.6 ml, 1:1, v/v) was added ammonium formate (20 mg) and 10% Pd/C (20 mg) and the reaction mixture was stirred at ambient temperature for 20 min. The mixture was filtered and water (3 ml) was added to the filtrate. The mixture was extracted with ethyl acetate (10 ml ×2). The solvent was removed in vacuo. To the residue were added acetonitrile (1 ml), triethylamine (1 ml) and water (1 ml) and the solution was stirred at ambient temperature for 1 h. The solvent was removed and the salt in the flask was washed away using water (2 ml×3). Ethyl ether was added and the solid product was collected and washed with more ether to afford a grey powder CP8-26 (16.8 mg, 54% yield): $^1$H NMR (acetone-d$_7$): 10.52 (br s, 1H, NH), 9.42 (br s, 1H, NH), 9.10 (br s, 1H, NH), 7.68–7.67 (d, 1H, J=1.5 Hz, Py-H), 7.40–7.39 (d, 1H, J=1.5 Hz, Py-H), 6.91–6.90 (m, 2H, C$_6$-H, Py-H), 6.73–6.72 (d, 1H, J=1.5 Hz, Py-H), 6.14 (s, 1H, C3H), 5.77–5.67 (m, 3H, CH$_2$OCH$_3$, CH$\underline{H}$OCH$_3$), 5.27–5.23 ( d, 1H, J=10.0 Hz, CHH$\underline{H}$OCH$_3$), 4.25–4.20 (dd, 1H, J=5.0, 11.0 Hz, NCHH), 4.12–4.08 (d, 1H, J=11.0 Hz, NCHH), 3.25 (s, 3H, OCH$_3$), 3.23 (s, 3H, OCH$_3$), 3.06–3.00 (m, 1H, CH$_2$CHCH$_2$), 2.25–2.20 (t, 2H, J=7 Hz, CH$_3$CH$_2$CH$_2$), 1.70–1.58 (m, 2H, CH$_3$CH$_2$CH$_2$), 1.40–1.37 (t, 1H, J=4.5 Hz, C8-HH), 0.93–0.88 (t, 3H, J=7 Hz, CH$_3$CH$_2$CH$_2$), FABHRMS calcd for C$_{30}$H$_{34}$N$_6$O$_6$H 575.2618, found 575.2646.

EXAMPLE 9

1, 2, 8, 8a-Tetrahydro-7-methyl-2-[4-(4 -butyramido-N-methoxymethylimidazole-2-carboxyamido)-N-methoxymethylimidazole-2-carboxy ]cyclopropa[c]-pyrrolo[3, 2-e]indole-4-(5H)-one (CP8-27.

Compound CP8-27 of the formula X, where R=0; Het= N-methoxymethylimidazole; m=2; n=0; A=butyramido, was prepared. 5-Benzyloxy-1-chloromethyl-8-methyl 3-[4-(4 -butyramido-N-methoxymethylimidazole-2-carboxyamido)-N-methoxymethylimidazole-2-carboxy ]-1, 2-dihydro-3H-pyrrolo [3, 2-e]indole (CP8-19) was synthesized using the same method as described for CP8-18 except that 4-(4-butyramido-N-methoxymethylimidazole-2 -carboxamido-)-N-methoxymethylimidazole-2-carboxylic acid CP8-13 was used in the yield of 69%: $^1$H NMR (CDCl$_3$): 10.65 (br s, 1H, NH), 9.03 (br s, 1H, NH), 8.28 (br s, 1H, NH), 7.82 (s, 1H, Im-H), 7.81 (s, 1H, Im-H), 7.66 (s, 1 H, C4-H), 7.47–7.36 (m, 5H, C$_6$H$_5$), 6.99 (s, 1H, C7-H), 5.84–5.68 (m, 4H, 2XCH$_2$OCH$_3$), 5.20–5.05 (dd, 2 H, J=11.0, 33.0 Hz, PhCH$_2$O), 4.89–4.85 (d, 1H, NCHH, J=11.5 Hz), 4.80–4.74 (dd, 1H, J=7.5, 11.0 Hz, NCHH), 4.02–3.80 (m, 2H, CHHCl, CH$_2$ClCHCH$_2$), 3.47– 3.37 (m, 4H, CHHCl, OCH$_3$), 3.30 (s, 3 H, OCH$_3$), 2.50–2.40 (t, 2H, J=7Hz, CH$_3$CH$_2$CH$_2$), 2.40 (s, 3H, ARCH$_3$), 1.87–1.74 (m, 2H, CH$_3$CH$_2$CH$_2$), 1.05–1.0 (t, 3H, J=7 Hz, CH$_3$CH$_2$CH$_2$), FABHRMS calcd for C$_{35}$H$_{39}$N$_8$O$_6$ClH 703.2759, found 703.2718.

CP8-27 was synthesized from CP8-9 (30 mg, 42 umol) using a similar method as described for CP8-26 as a grey powder (17.8 mg, 72% yield): $^1$H NMR (acetone-d$_6$): 10.58 (br s, 1H, NH), 9.51 (br s, 1H, NH) , 9.48 (br s, 1H, NH), 7.72 (s, 1H, Im-H), 7.65 (s, 1H, Im-H), 6.93–6.92 (m, 1H, C6-H), 6.81 (br s, 1H, C3-H), 5.88 (s, 3H, CH$_2$OCH$_3$), 5.77–5.62 (dd, 2H, J=11.0, 32.0 Hz, CH$_2$OCH$_3$), 4.69–4.65 (d, 1H, J=11.0 Hz, NCHH), 4.51–4.46 (dd, 1H, J=5.0, 11.0 Hz, NCHH), 3.36 (s, 3H, OCH$_3$), 3.33 (s, 3H, OCH$_3$), 3.12–3.07 (m, 1H, CH$_2$CHCH$_2$), 2.43– 2.38 (t, 2H, J=7Hz, CH$_3$CH$_2$CH$_2$), 2.20–2.17 (dd, 1H, J=4.5, 7.5 Hz, C8HH), 1.76–1.63 (m, 2H, CH$_3$CH$_2$CH$_2$), 1.33–1.29 (t, 1H, J=4.5 Hz, C8-HH), 0.98–0.93 (t, 3H, J=7 Hz, CH$_3$CH$_2$CH$_2$) , FABHRMS calcd for C$_{30}$H$_{34}$N$_6$O$_6$H 577.2523, found 577.2523.

EXAMPLE 10 cytotoxicity

KB human nasopharyngeal carcinoma cells, were maintained in RPMI 1640 medium supplemented with 10% fetal bovine serum. KB cells were cultured in plastic tissue culture flasks and kept in an incubator at 37° C. in humidified air containing 5% CO$_2$. These cells were free of Mycoplasma as determined with Hoechst 33258 stain.

The antiproliferative effect of compounds was determined using cell staining method by crystal violet.

One hundred-µl cultures were established at 10$^3$ cells/ well in 96-well tissue culture plates (Nunc, Roskilde, Denmark). After 24 h. 100 µl of the medium containing 2 times concentrated the compounds were added to the cell culture. After an additional 3 days culture, cells were fixed to 20 µl of 25% glutaraldehyde for 15 minutes and washed with water, dried and stained with 0.05% crystal violet in 20% methanol for 15 minutes. After washing with water and drying, crystal violet was extracted with 100µl of 50 mM NaH$_2$PO$_4$/ethanol (1:1 v/v) and OD$_{540}$ was measured by the multiscanphotometer (Corona, Tokyo, Japan). A linear relationship between cell number and the amount of dye binding was found over the range of cell densities observed all experiments. The concentration of compound that resulted in 50% of the absorbance of untreated cultures was determined by linear regression of the data.

EXAMPLE 11

Antitumor Efficacy

All compounds were dissolved in dimethyl sulfoxide (DMSO), diluted in sterile 0.9% NaCl solution to 5% final DMSO concentration. BALB/c X DBA/2F1 (CDF1) mice were purchased from Japan CLEA. P388 lymphocytic leukemia cells were inoculated intraperitoneally (10$^6$ cells) 1 day prior to treatment into 6 week-old male CDF$_1$ mice, and compounds were injected intraperitoneally in a total volume of 0.1 ml/10g mouse body weight. Efficacy for these models was expressed as the Increase in life span (ILS) of treated mice in comparison to untreated tumor-bearing mice. Maximum ILS obtained was shown in Table 4. Experiment was completed on day 30 after tumor inoculation, and survivor on that day was evaluated as cured animal. Time to death (mean±SD.n=9) for untreated animals was 11.5±1.2 day and for solvent treated animals was 11.7±2.1 day.

We claim:

1. Compounds of the formula:

wherein,

Het$^1$ and Het$^2$ are individually selected from the group consisting of pyrrole, imidazole, N-alkylimidazole, N-alkoxymethylimidazole, thiophene, thiophene, furan, thiazole, oxazole, N-alkylpyrrole, N-alkoxymethylpyrrole and pyrazole, R is selected from the group consisting of a valence bond; a divalent C$_1$–C$_6$ alkyl; a divalent C$_2$–C$_6$ alkenyl; a divalent C$_2$–C$_6$ alkynyl; a divalent cycloalkane of formula C$_p$H$_{2p-2}$ wherein p is 3 to 7; and an ortho, meta or para linked aromatic group, A is selected from the group consisting of a C$_1$–C$_6$ alkyl group; an amidine or derivative thereof; a guanidine; a secondary, tertiary or quaternary ammonium salt; and a sulfonium salt, n is 0 to 3, and m is 0 to 3, wherein when n=0, m is 1–3.

2. The compounds according to claim 1, wherein R is selected from the group consisting of (CH$_2$)$_{1-6}$ —CH=CH—, E or Z; and —C≡C—.

3. The compound according to claim 1, wherein said aromatic group is selected from the group consisting of phenyl and naphthyl.

4. The compounds according to claim 1, wherein R is a divalent cycloalkane of formula C$_p$H$_{2p-2}$ wherein p is 3 to 7.

5. The compounds according to claim 1, wherein $Het_1$ and $Het_2$ are both N-alkylpyrrole, wherein the alkyl contains 1 to 4 carbon atoms.

6. The compounds according to claim 1, wherein $Het_1$ and $Het_2$ are both N-alkoxymethylpyrrole, wherein the alkoxy contains 1 to 4 carbon atoms.

7. The compounds according to claim 1, wherein $Het_1$ and $Het_2$ are both N-alkylimidazole, wherein the alkyl contains 1 to 4 carbon atoms.

8. The compounds according to claim 1, wherein $Het_1$ and $Het_2$ are both N-alkoxymethylimidazole, wherein the alkoxy contains 1 to 4 carbon atoms.

9. The compounds according to claim 1, wherein $Het^1$ and $Het^2$ are individually selected from the group consisting of thiophene, furan, thiazole, oxazole, N-alkylpyrrole, imidazole, pyrazole and triazole, wherein said alkyl group contains 1 to 4 carbon atoms.

10. The compounds according to claim 1, wherein $Het^1$ and $Het^2$ are individually selected from the group consisting of thiophene, furan, thiazole, oxazole, N-alkoxymethylpyrrole, imidazole, pyrazole, and triazole, wherein said alkoxy group contains 1 to 4 carbon atoms.

11. The compounds according to claim 1, wherein A is a straight chain alkyl group of 1 to 6 carbon atoms.

12. The compounds according to claim 1, wherein A is an amidine, with an aliphatic chain, of the formula wherein r is 0 to 5 and X is selected from the group consisting of —H, —OH, —$NH_2$, —$CH_3$, —$CH_2CH_3$, and $C_3H_7$.

13. The compounds according to claim 1, wherein A is an amidine, wherein at least one nitrogen atom is a member of a five-membered heterocyclic structure.

14. The compounds according to claim 1, wherein A is a guanidine of formula wherein r=0 to 5 and X is selected from the group consisting of —H, —OH, —$NH_2$, —$CH_3$, $C_2H_5$ and $C_3H_7$.

15. The compounds according to claim 1, wherein A is a quaternary, tertiary or secondary ammonium salt of the formula wherein r=0 to 5 and q is 0, 1, 2, 3, and X is an alkyl or alkenyl group of 1 to 3 carbon atoms.

16. The compounds according to claim 1, wherein A is a sulfonium salt of formula $CrH_{2r}$—SXY, wherein r is 0 to 5 and X and Y are alkyl or alkenyl groups of 1 to 3 carbon atoms.

17. A pharmaceutical composition comprising a compound of the formula:

wherein, $Het^1$ and $Het^2$ are individually selected from the group consisting of pyrrole, imidazole, N-alkylimidazole, N-alkoxymethylimidazole, triazole, thiophene, furan, thiazole, oxazole, N-alkylpyrrole, N-alkoxymethylpyrrole and pyrazole, R is selected from the group consisting of a valence bond; a divalent $C_1$–$C_6$ alkyl; a divalent $C_2$–$C_6$ alkenyl; a divalent $C_2$–$C_6$ alkynyl; a divalent cycloalkane of formula $C_pH_{2p-2}$ wherein p is 3 to 7; and an ortho, meta or para linked aromatic group,

A is selected from the group consisting of a $C_1$–$C_6$ alkyl group; an amidine or derivative thereof; a guanidine; a secondary, tertiary or quaternary ammonium salt; and a sulfonium salt, n is 0 to 3, and m is 0 to 3, wherein when n=0, m is 1–3, in combination with a pharmaceutically acceptable carrier.

18. A method for alkylating specific DNA sequences in vivo, comprising administering to a patient in need of such alkylating, an amount of a compound of the formula:

wherein, $Het^1$ and $Het^2$ are individually selected from the group consisting of pyrrole, imidazole, N-alkylimidazole, N-alkoxymethylimidazole, triazole, thiophene, furan, thiazole, oxazole, N-alkylpyrrole, N-alkoxymethylpyrrole and pyrazole, R is selected from the group consisting of a valence bond; a divalent $C_1$–$C_6$ alkyl; a divalent $C_2$–$C_6$ alkenyl; a divalent $C_2$–$C_6$ alkynyl; a divalent cycloalkane of formula $C_pH_{2p-2}$ wherein p is 3 to 7; and an ortho, meta or para linked aromatic group, A is selected from the group consisting of a $C_1$–$C_6$ alkyl group; an amidine or derivative thereof; a guanidine; a secondary, tertiary or quaternary ammonium salt; and a sulfonium salt, n is 0 to 3, and m is 0 to 3, wherein when n=0, m is 1–3, effective to alkylate specific DNA sequences.

19. The method according to claim 18, wherein said DNA sequences are oncogene DNA sequences.

20. A method of treating solid and blood-borne cancers selected from the group consisting of nasopharyngeal tumors and lymphocytic leukemia comprising administering to a patient in need of such treatment, an amount of a compound of the formula:

$$N-CO-R+Het^1NHCO)_n-(Het^2NHCO)_mA,$$

wherein,

Het$^1$ and Het$^2$ are individually selected from the group consisting of pyrrole, imidazole, N-alkylimidazole, N-alkoxymethylimidazole, triazole, thiophene, furan, thiazole, oxazole, N-alkylpyrrole, N-alkoxymethylpyrrole and pyrazole, R is selected from the group consisting of a valence bond; a divalent $C_1$–$C_6$ alkyl; a divalent $C_2$–$C_6$ alkenyl; a divalent $C_2$–$C_6$ alkynyl; a divalent cycloalkane of formula $C_pH_{2p-2}$ wherein p is 3 to 7; and an ortho, meta or para linked aromatic group, A is selected from the group consisting of a $C_1$–$C_6$ alkyl group; an amidine or derivative thereof; a guanidine; a secondary, tertiary or quaternary ammonium salt; and a sulfonium salt, n is 0 to 3, and m is 0 to 3, wherein when n=0, m is 1–3, effective to treat said solid and blood-borne cancers.

* * * * *